United States Patent [19]

Schulze et al.

[11] Patent Number: 5,065,929
[45] Date of Patent: Nov. 19, 1991

[54] SURGICAL STAPLER WITH LOCKING MEANS

[75] Inventors: Dale R. Schulze, Lebanon; Jon A. Sherman; W. Michael Mereness, both of Cincinnati, all of Ohio

[73] Assignee: Ethicon, Inc., Somerville, N.J.

[21] Appl. No.: 678,919

[22] Filed: Apr. 1, 1991

[51] Int. Cl.⁵ ............................................. A61B 17/04
[52] U.S. Cl. ..................................... 227/19; 227/175; 227/180
[58] Field of Search ............... 227/175, 176, 180, 181, 227/182, 19, 120, 135, 901

[56] References Cited

U.S. PATENT DOCUMENTS

| 4,429,695 | 2/1984 | Green | 227/180 |
| 4,605,001 | 8/1986 | Rothfuss et al. | 227/19 |
| 4,863,088 | 9/1989 | Redmond et al. | 227/19 |
| 4,991,764 | 2/1991 | Mericle | 227/180 |

Primary Examiner—Mark Rosenbaum
Assistant Examiner—Allan M. Schrock
Attorney, Agent, or Firm—Jason Lipow

[57] ABSTRACT

The present invention relates to an improved two-piece surgical stapler having first and second mated pieces, and including a first and a second locking means that insure that the two pieces are mated when staples are being ejected.

3 Claims, 8 Drawing Sheets

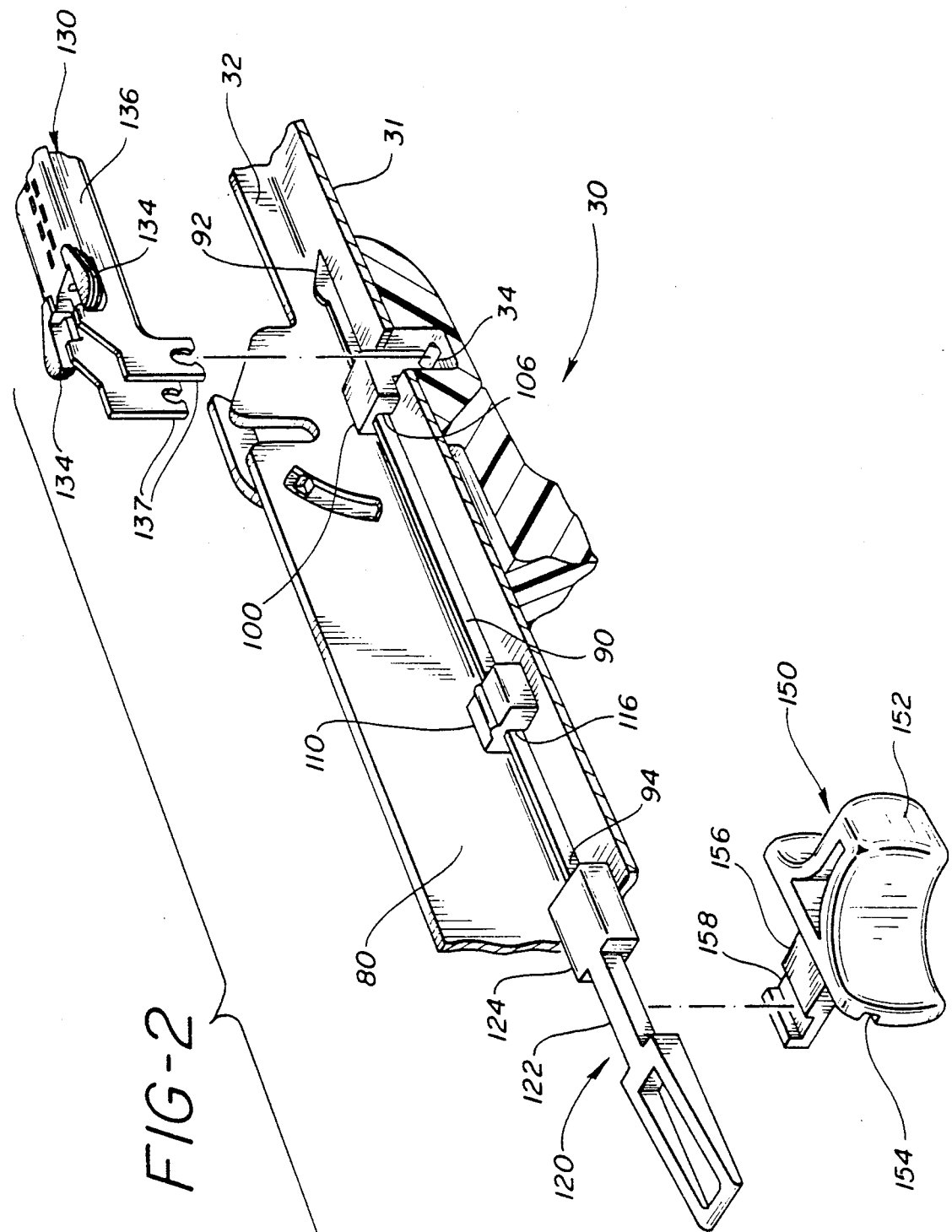

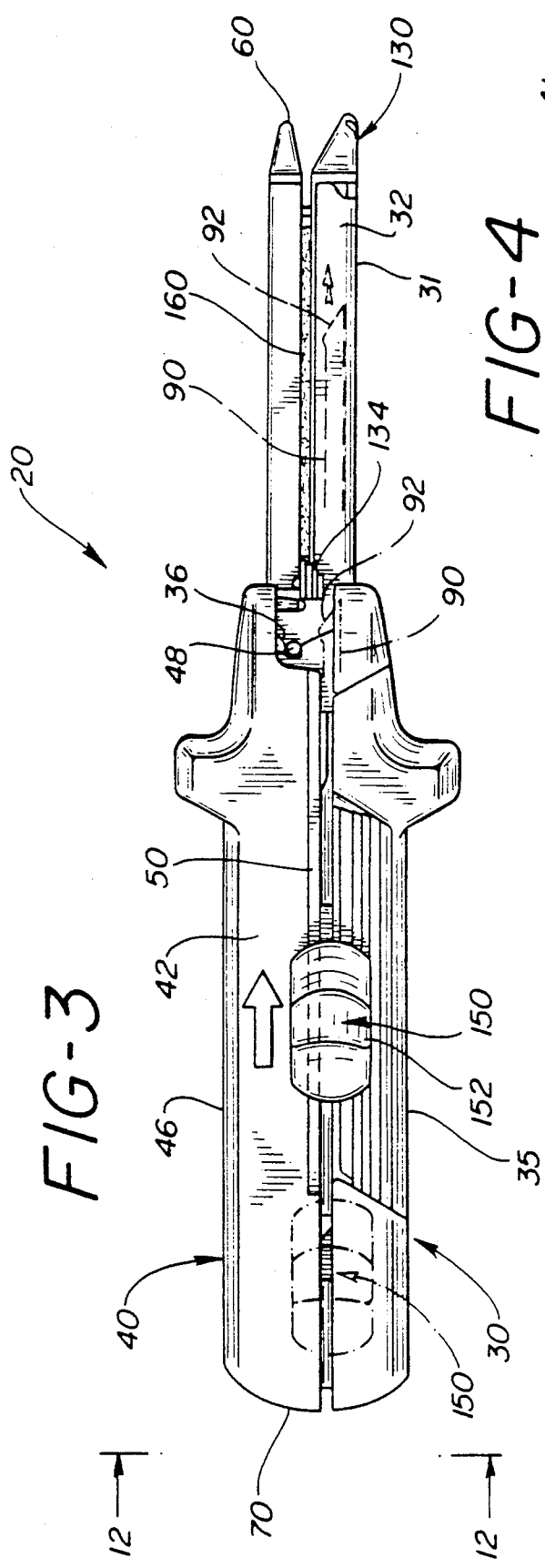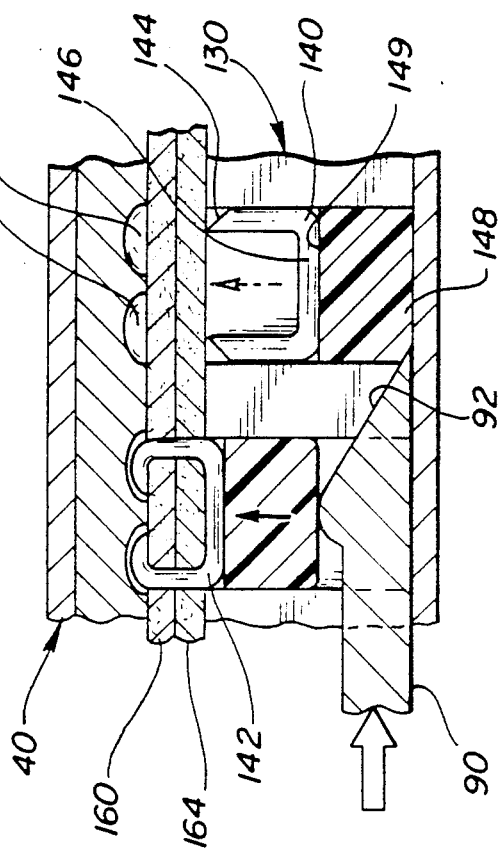

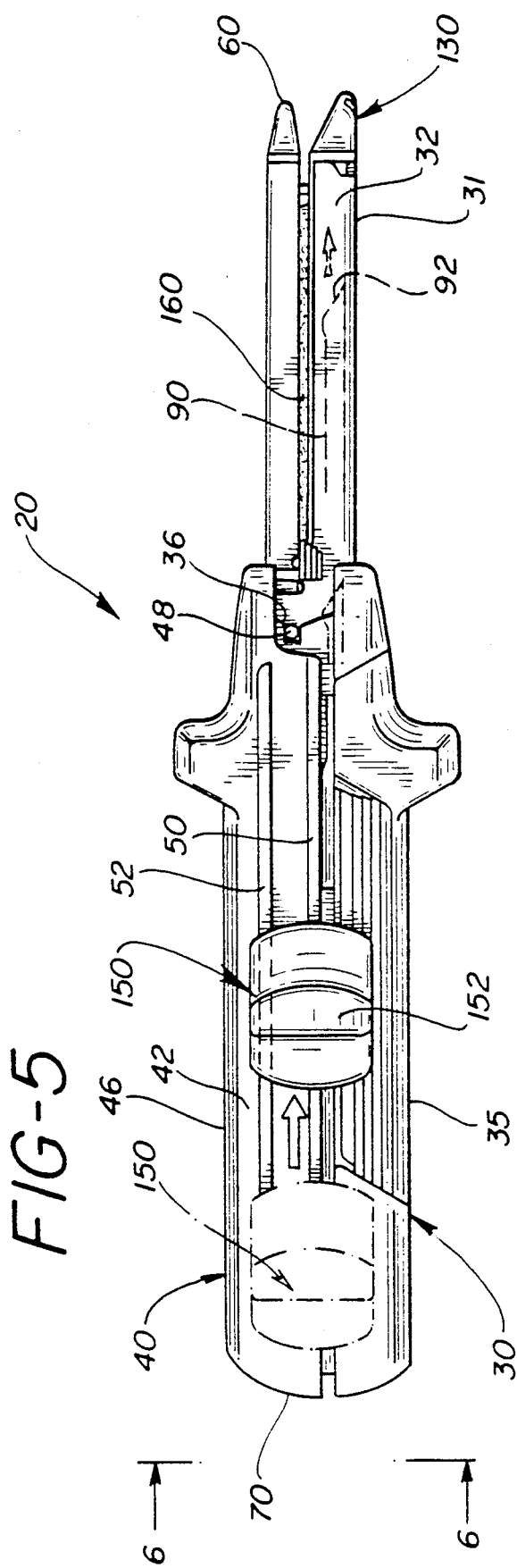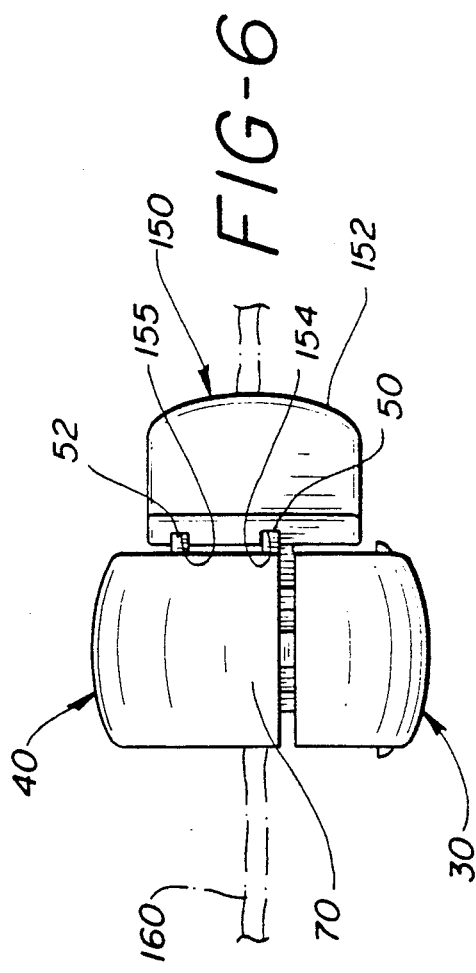

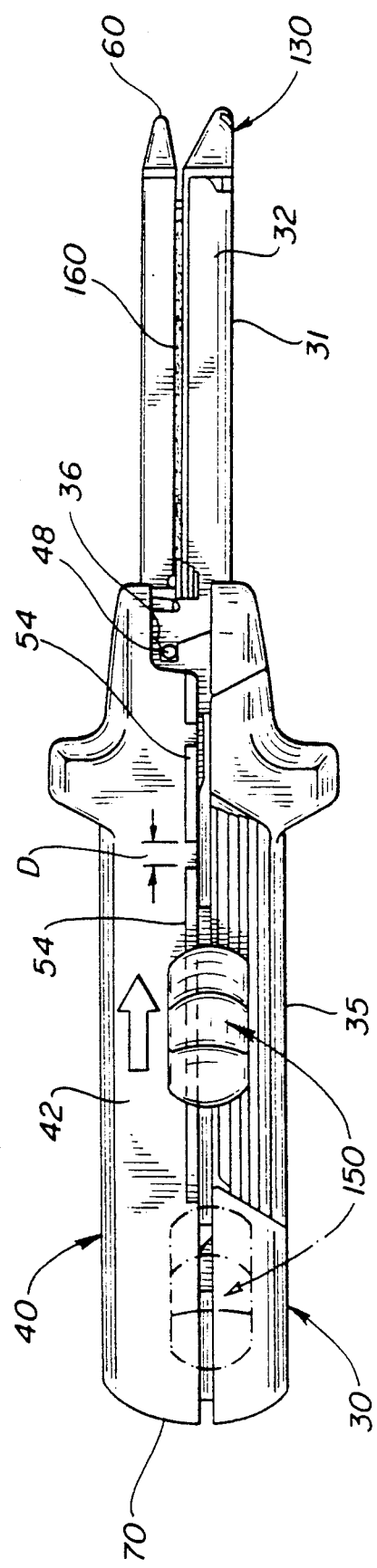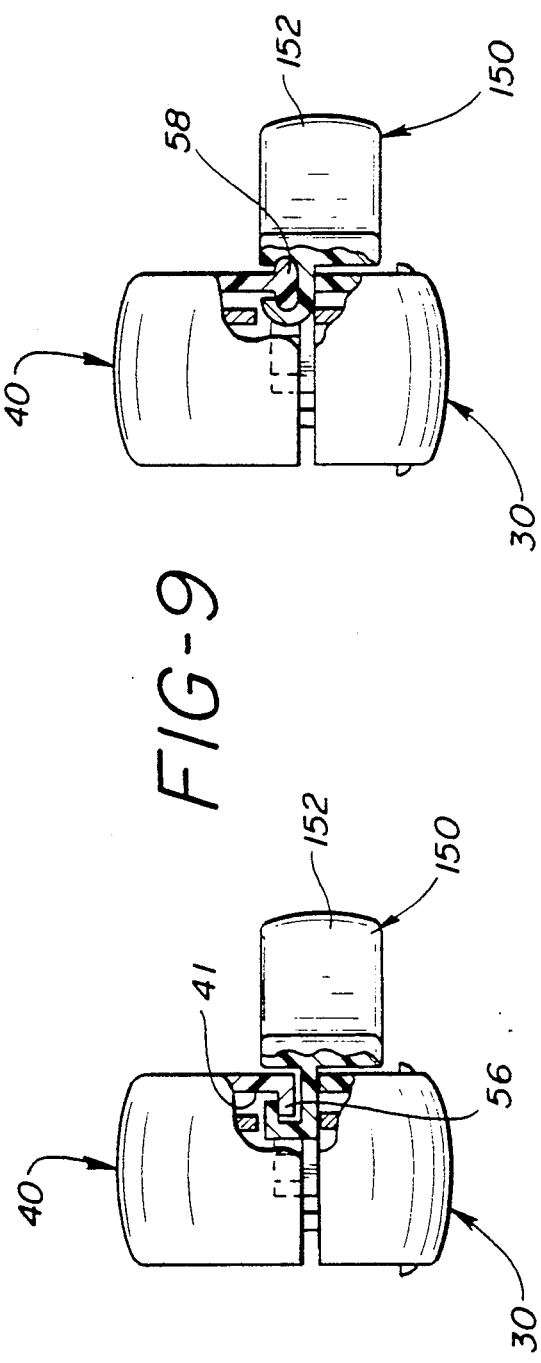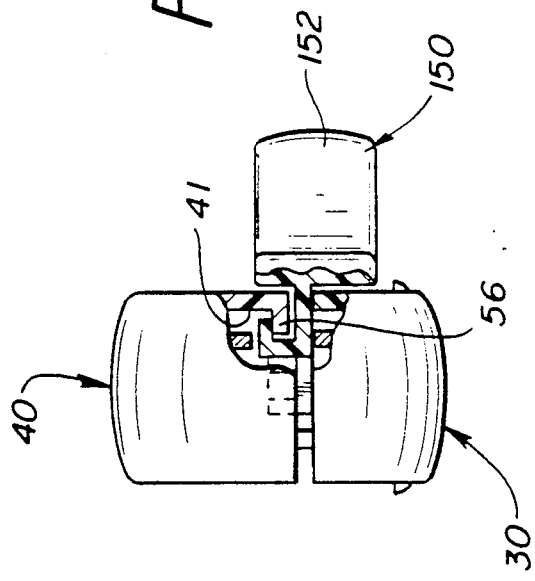

SURGICAL STAPLER WITH LOCKING MEANS

FIELD OF THE INVENTION

The present invention relates to an improved two-piece linear surgical stapler having first and second mated pieces, and including first and second locking means that insure that the first and second pieces are mated when staples are being ejected.

BACKGROUND OF THE INVENTION

The introduction of surgical staplers has greatly facilitated the art of closing the tissue of surgical patients and, in particular has greatly decreased the time required by the surgeon to Perform this task. Several useful versions of such devices are now known such as those disclosed in U.S. Pat. Nos. 4,608,981 issued to Rothfuss et al. on Sept. 2, 1986; 4,633,874 issued to Chow et al. on Jan. 6, 1987; and 4,892,244 issued to Fox et al. on Jan. 9, 1990.

The design of present staplers reflect the desire for speed and efficiency. Accordingly, such staplers commonly are designed in two pieces wherein the pieces may be separated to accommodate the insertion of a disposable staple cartridge and allow the user to quickly reload the device during a surgical procedure. Typically, one piece contains the staple cartridge including staples having sharp ends and the other piece includes an anvil against which the staple ends are clinched when tissue is being stapled. If the first and second pieces are not mated during stapling then the staple ends will not be clinched against the anvil. As a result patients will have sharp staple ends projecting upward from their tissue. This potentially dangerous situation illustrates how important it is for the first and second pieces to be mated when staples are being ejected.

In recognition of this problem, mechanisms to lock the mated first and second pieces have been devised. Unfortunately, Present locking mechanisms for linear staplers that are divided longitudinally into first and second pieces do not insure that the first and second pieces are mated when staples are being ejected.

One such stapler, described in U.S. Pat. No. 4,633,874, includes a pivotable C-shaped member affixed to a first piece and a stationary locking pin affixed to a second piece. The C-shaped member is pivotable between a first and a second position and engages and disengages the locking pin when moved into said respective positions to lock and unlock the two pieces.

While this locking mechanism, when engaged, will lock the two pieces together, it does not insure that the first and second pieces are mated when staples are being ejected because staples may be ejected whether the C-shaped member is in the first (unlocked) position or the second (locked) position. Accordingly, if the locking mechanism becomes disengaged during use or if the user neglects to engage the mechanism prior to use then, disadvantageously, staples may still be ejected from the unlocked stapler.

Consequently, there is a need for a two-piece surgical stapler, having locking means that insure that the first and second pieces are mated when staples are being ejected.

SUMMARY OF THE INVENTION

In accordance with the present invention a surgical stapler is divided longitudinally into first and second mated pieces. The stapler has a staple ejecting end and an opposite end and comprises a longitudinal inner passage. A staple ejecting means is slidably affixed to the first piece and is adapted to move longitudinally within the passage toward the staple ejecting end in order to eject staples therefrom. Additionally, the staple ejecting means is integral with a gripping means that projects out of the first piece and is for gripping and moving the ejecting means within the passage. The gripping means is provided with a first locking means and a second locking means is affixed to the second piece. The first locking means is adapted to engage the second locking means when the user grips the gripping means to move the integral ejecting means within the passage toward the ejecting end. Accordingly, when the staple ejecting means is moved toward the ejecting end to eject staples, the first locking means engages the second locking means and insures that the pieces are mated when staples are being ejected.

In a preferred embodiment the second locking means is a ridge extending parallel to the inner passage and the first locking means is a groove aligned with the ridge.

In another preferred embodiment the second locking means is a Plurality of spaced, aligned ridges. The distances between adjacent pairs of ridges is less than the length of the groove that is aligned with the ridges.

BRIEF DESCRIPTION OF THE DRAWINGS

FIG. 2 is an exploded perspective view of the first piece of this invention with parts of the first piece broken away;

FIG. 3 is a side elevational view of the assembled stapler of FIG. 1;

FIG. 4 is a schematic and cross-sectional view of the stapler of this invention illustrating staple ejection;

FIG. 5 is a side elevational view of another embodiment of the present invention;

FIG. 6 is an end view as seen along view line 6—6 of FIG. 5;

FIG. 7 is a side elevational view of another embodiment of the present invention;

FIG. 8 is an end view of yet another embodiment of the present invention;

FIG. 9 is an end view of another embodiment of the present invention;

DETAILED DESCRIPTION OF SPECIFIC EMBODIMENTS

Figure 1:
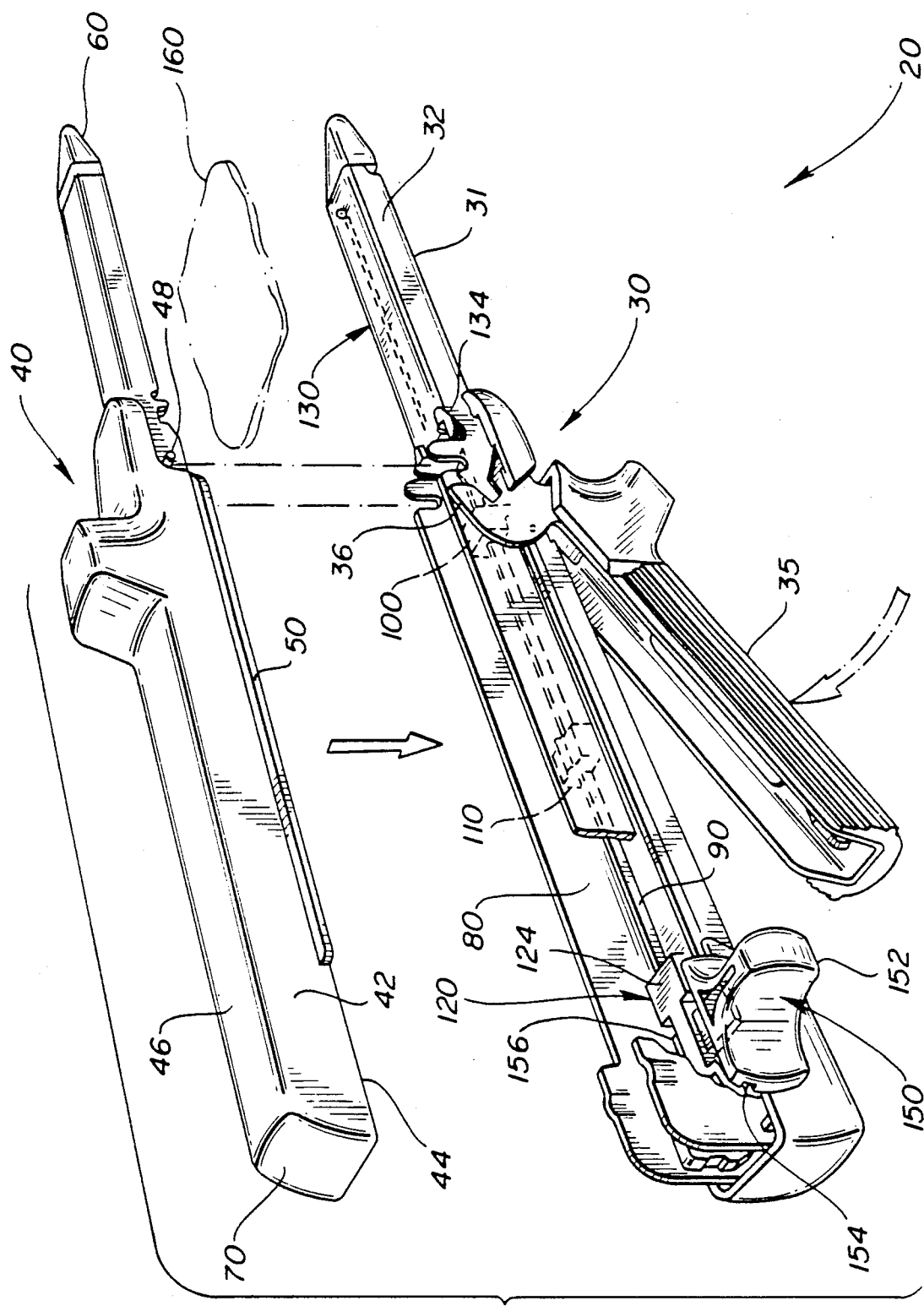
FIG. 1 is an exploded perspective view of a stapler of this invention with the first and second pieces disengaged prior to use and with parts of the first piece broken away.
Figure 10:
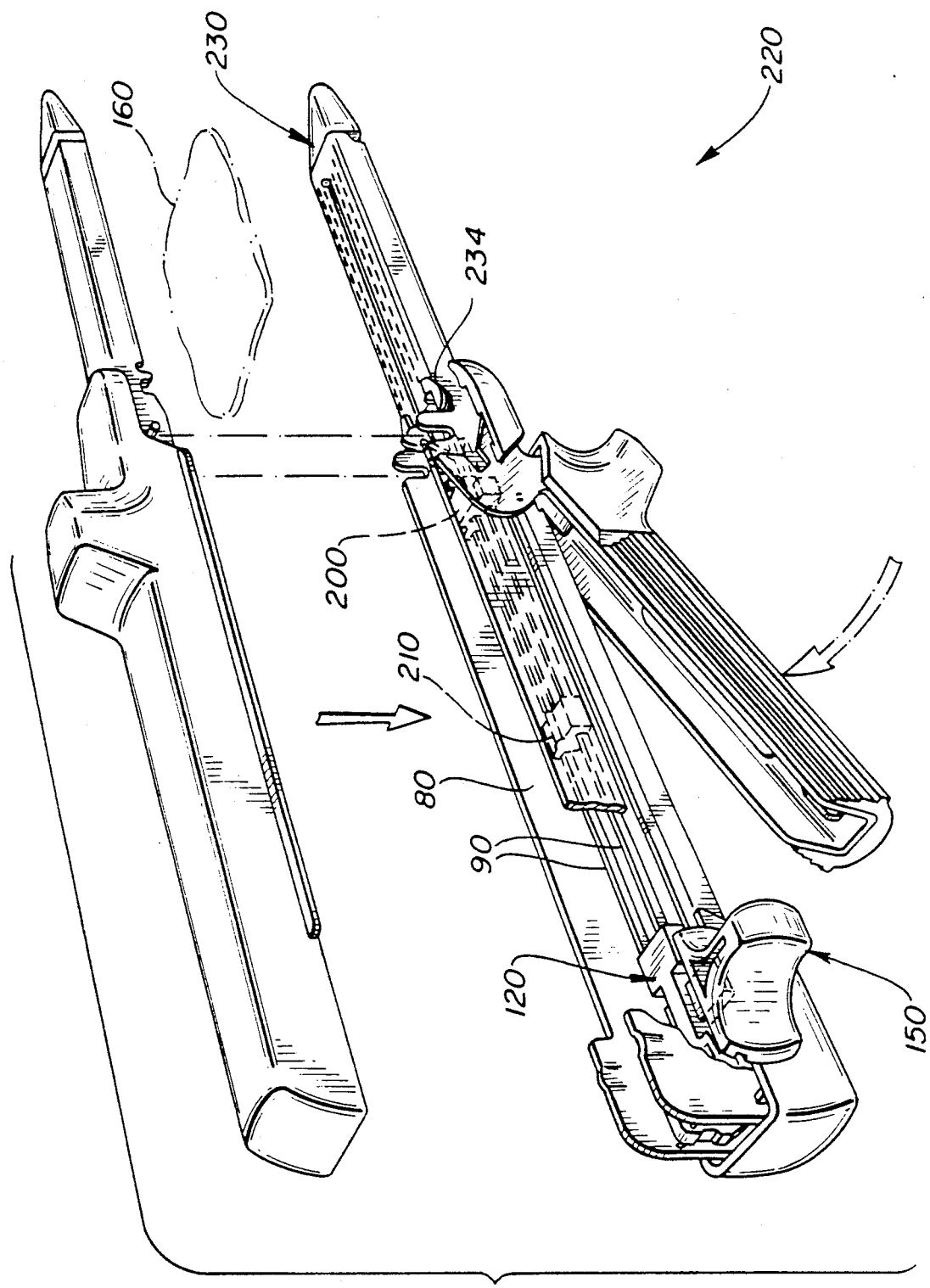
FIG. 10 is an exploded perspective view of another embodiment of the stapler of this invention with the first and second pieces disengaged prior to use and with parts of the first piece broken away.

Reference will now be made in detail to specific embodiments of the present invention which are conveniently described by reference to the accompanying FIGS. 1-12.

As seen in FIGS. 1-4 and FIG. 12, a surgical stapler 20 of this invention is divided longitudinally into a first piece 30 and a second piece 40 and has a staple ejecting end 60 and an opposite end 70. Stapler 20 has a longitudinal inner passage 80.

FIG. 2 illustrates a staple ejecting means, pusher bar 90 which has a ramp 92 integral with its staple ejecting end and an opposite end 94. A movable end portion 120 includes a narrow end portion 122 and a widened end portion 124, which is integral with opposite end 94. Pusher bar 90 is slidably affixed to first piece 30 and adapted to move longitudinally within passage 80 toward staple ejecting end 60 in order to eject staples 140 (seen in FIG. 4) from a staple cartridge 130.

A stationary stabilizer 100 and a movable stabilizer 110 are both affixed to first piece 30 in between ramp 92 and end portion 120. Movable stabilizer 110 includes a pusher bar slit 116 aligned with a pusher bar slit 106 of stationary stabilizer 100 that accommodates pusher bar 90 so that pusher bar 90 may slide through both slits.

A gripping means 150 includes an external portion 152 projecting out of first piece 30 for gripping and an internal portion 156 having a cavity 158 that is matable with narrow end portion 122. The narrow end portion 122 is affixed to cavity 158 so that moving external portion 152 moves end portion 120 which in turn moves pusher bar 90 toward staple ejecting end 60 within passage 80.

Stapler 20 of FIG. 2 includes staple cartridge 130 within first piece 30. Specifically, parallel side walls 136 of staple cartridge 130 fit within lower jaw channel 32 of lower jaw portion 31. Two pairs of legs 137 secure staple cartridge 130 to first piece 30 by engaging cylinder 34 of first piece 30. To facilitate removal of the cartridge 130 from first piece 30, staple cartridge 130 also has two wing-like pieces 134 extending generally perpendicularly away from the upper surface of parallel side walls 136.

Staple cartridge 130 houses staples 140 that have two sharp staple ends 144 and a staple head 146 that bears against a surface 149 of a driver 148. FIG. 4 illustrates a staple 140 before it is ejected and clinched, as is staple 142. Staple 140 is ejected when ramp 92 of pusher bar 90 slides under driver 148 and pushes driver 148 upward against staple head 146. Second piece 40 includes an anvil 41 against which the staple ends 144 are clinched when tissue layers 160 and 164 are being stapled. This is accomplished as gripping means 150 is moved toward the staple ejecting end 60.

Figure 12:
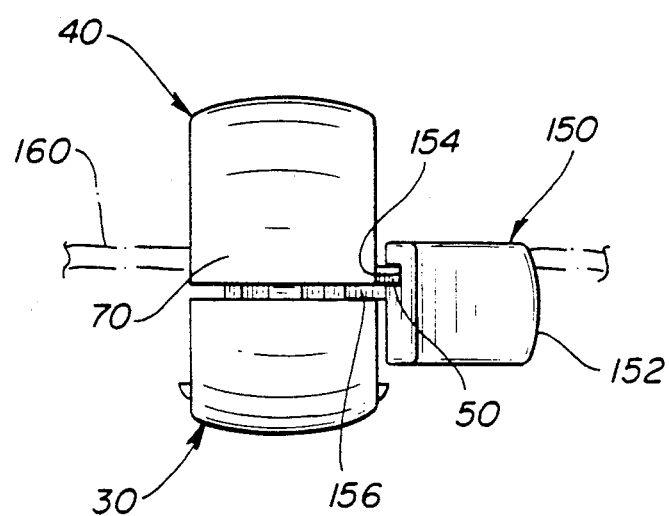
FIG. 12 is an end view as seen along view line 12—12 of FIG. 3.

A ridge 50 is affixed to the external surface 42 of first piece 40. Gripping means 150 is provided with a first locking means in the form of a groove 154 adapted to engage a second locking means in the form of ridge 50 when pusher bar 90 is moved within inner passage 80 toward the ejecting end 60. When pusher bar 90 is moved toward ejecting end 60 to eject staples 140, the groove 154 engages ridge 50 and insures that the first and second pieces, 30 and 40, respectively, are mated when staples 140 are being ejected. FIG. 12 best illustrates how groove 154 engages ridge 50.

The operation of this surgical stapler is similar to the operation of the surgical stapler disclosed in copending patent application (Ser. No. 620,119), commonly assigned U S. Pat. No. 4,608,981, (Rothfuss et al.), issued Sept. 2, 1986, U.S. Pat. No. 4,633,874 (Chow et al.), issued Jan. 6, 1987, and U.S. Pat. No. 4,892,244, (Fox et al.), issued Jan. 9, 1990, all hereby incorporated by reference.

The embodiment of this invention illustrated in FIG. 1 also illustrates a clamping mechanism employed to decrease the amount of force that a user must exert in order to clamp tissue layer 160 in between lower jaw portion 31 and anvil 41. The first piece 30 includes a pivotable clamping portion 35, pivotable between a first and a second position, and lower jaw portion 31. In the first position the pivotable clamping portion 35 is positioned at an oblique angle to lower jaw portion 31. During the first position a C-shaped member 36 of pivotable clamping portion 35 is disengaged from a stationary clamping pin 48 that is affixed to second piece 40. On the other hand, in the second position C-shaped member 36 engages the stationary clamping pin 48, thereby clamping tissue 160 in between first and second pieces 40 and 30. In the second position, pivotable clamping portion 35 is essentially parallel to lower jaw portion 31. As long as C-shaped member 36 engages stationary clamping pin 48 tissue layer 160 is effectively clamped between lower jaw portion 31 and anvil 41.

The first and second locking means, groove 154 and ridge 50, that insure that the first and second pieces are mated when staples 140 are being ejected may be embodied in many different forms. In FIGS. 1, 3, 5 and 6 the second locking means includes a ridge 50 that is affixed to external surface 42 on the right side of the stapler 20 as seen from opposite end 70. However, stapler 20 may be turned so that external surface 42 is the top, left side or bottom of stapler 20. Furthermore, FIG. 9 illustrates ridge 58, integral with bottom surface 44. Likewise, a ridge integral with the top surface 46 of external surface 42 can be the second locking means. While ridge 50 is affixed to external surface 42 in the embodiment shown in FIGS. 1, 3, 5 and 6, in FIG. 8 there is illustrated a ridge 56 affixed to internal surface 41. As will be described below, there can be many different types of ridges.

The dimensions of ridge 50 itself are not critical; provided however that the overall dimensions of groove 154 must be greater than those of ridge 50 so that ridge 50 fits within groove 154 while at the same time fitting tightly enough to perform the locking function.

Ridge 50, a continuous longitudinally extending ridge, is best illustrated in FIG. 1. Ridge 50 is affixed to external surface 42 at a Position adjacent bottom surface 44 of second piece 40. However, it is understood that ridge 50 may be affixed to second piece 40 at a position adjacent the top surface of second piece 40, or at any position in between.

Furthermore, the ridge need not be continuous. FIG. 7 illustrates that the second locking means may be spaced aligned ridges 54 as long as the distance "D" between each pair of ridges 54 is less than the entire length of groove 154. If the length of groove 154 is greater than the length of distance "D" between each pair of ridges 54 then groove 154 will engage at least a portion of ridges 54 and insure that second piece 40 and first piece 30 are mated when staples 140 are being ejected.

Another embodiment of the present invention is illustrated in FIGS. 5 and 6. This embodiment has a plurality of parallel ridges 50 and 52 and a plurality of parallel grooves 154 and 155, that are aligned with ridges 50 and 52 as well as being adapted to engage them. These ridges 50 and 52 and grooves 154 and 155 are parallel to the inner passage 80. Clearly however, when the combination of ridges and grooves becomes more complex the manufacturing of such staplers becomes more expensive.

Further still, the location of the first and second locking means may be reversed e.g., groove 154 is on the second piece and ridge 50 is on the first piece.

Figure 11:
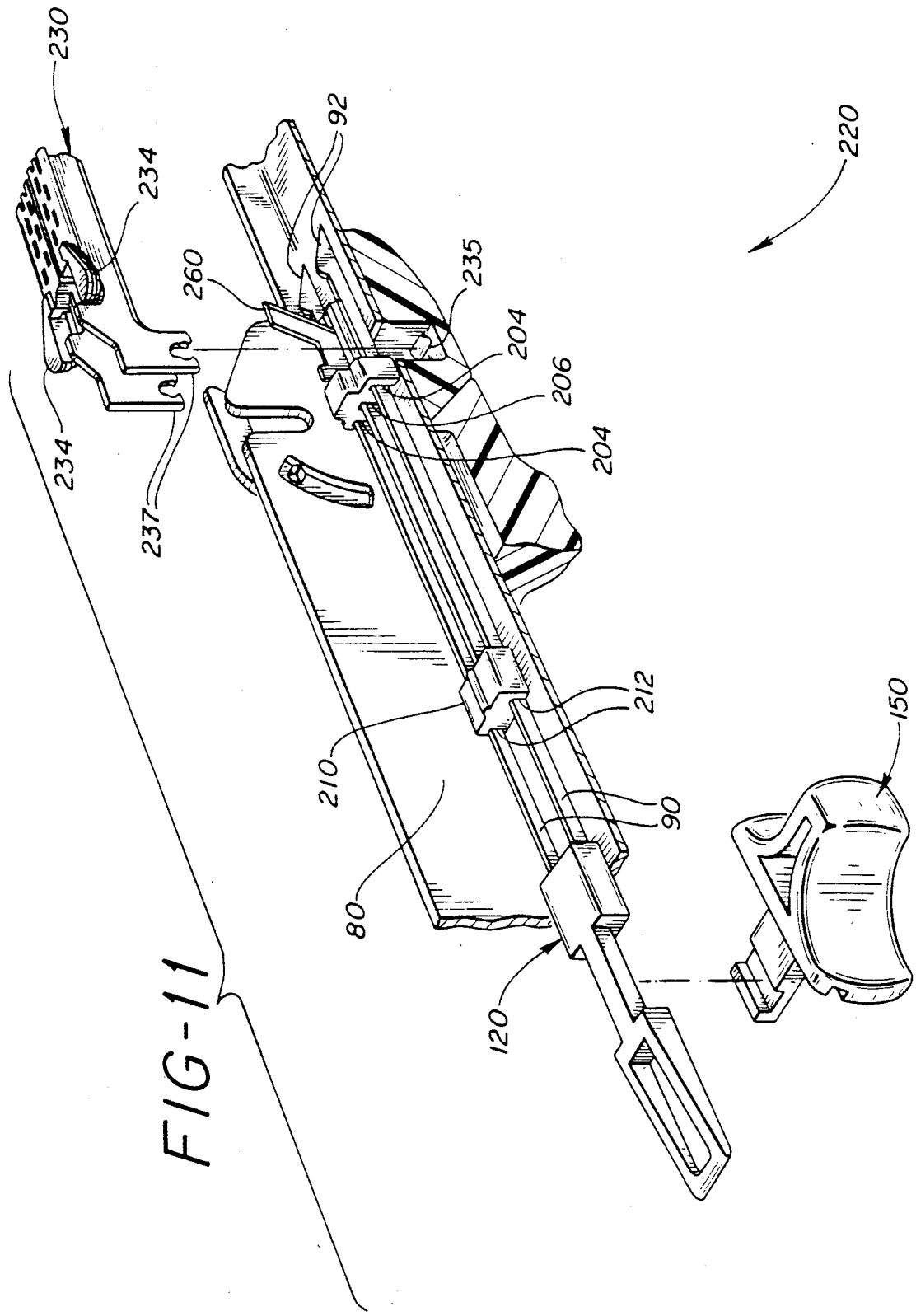
FIG. 11 is an exploded perspective view of the first piece of the FIG. 10 embodiment of this invention with parts of the first piece broken away.

FIG. 11 illustrates another embodiment of the stapler of the present invention that includes the same gripping means 150 and end portion 120 as stapler 20 does. Instead of having one pusher bar 90 stapler 220 includes two. The main difference between these two embodiments is that stapler 220 includes a knife blade assembly 260 and the inclusion of knife blade assembly 260 necessitates changes in the structure of the staple cartridge, stationary stabilizer, and movable stabilizer.

Accordingly, the embodiment illustrated in this FIG. 11 includes staple ejecting means comprising two pusher bars 90 adapted to eject staples from staple cartridge 230. Movable stabilizer 210 is provided with slits 212 to accommodate the two pusher bars. Similarly, stationary stabilizer 200 is provided with slits 204 to accommodate the pusher bars and, additionally, is provided with slit 206 to accommodate the knife assembly 260. The pusher bars terminate at the ejection end of the stapler in ramps 92 which operate in the same manner as in the prior discussed embodiment to eject staples 140. Staple cartridge 230 is provided with gripping wings 234 and legs 237 which engage cylinder 235 thereby securing staple cartridge 230 to stapler 220.

What is claimed is:

1. A surgical stapler divided longitudinally into first and second mated pieces and having a staple ejecting end and an opposite end, said stapler comprising:
   a longitudinal inner passage;
   a staple ejecting means slidably affixed to said first piece and adapted to move longitudinally within said passage toward the staple ejecting end to eject staples therefrom;
   said staple ejecting means being integral with a gripping means projecting out of said first piece for gripping and moving said ejecting means within said passage;
   said gripping means provided with a first locking means;
   said second piece provided with a second locking means;
   said first locking means adapted to engage said second locking means when said ejecting means is moved within said passage toward said ejecting end;
   whereby when said staple ejecting means is moved toward said ejecting end to eject staples, said first locking means engages said second locking means and insures that said pieces are mated when staples are being ejected.

2. The surgical stapler according to claim 1 wherein said second locking means is a ridge extending parallel to said ejecting end of the inner Passage that is affixed to the external surface of said second piece and said first locking means is a groove aligned with said ridge.

3. The surgical stapler according to claim 1 wherein said second locking means is a plurality of spaced, aligned ridges extending parallel to said inner passage and said first locking means is a groove aligned with said ridges, said ridges being spaced such that the distance between each pair of said ridges is less than the length of said groove.

* * * * *